(12) United States Patent
Dang et al.

(10) Patent No.: US 10,638,945 B2
(45) Date of Patent: May 5, 2020

(54) TRANSDERMAL SENSING PROBES AND SMART PATCH SYSTEMS USING SAME

(71) Applicant: International Business Machines Corporation, Armonk, NY (US)

(72) Inventors: Bing Dang, Chappaqua, NY (US); Yang Liu, Ossining, NY (US); Steven L. Wright, Cortlandt Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 725 days.

(21) Appl. No.: 15/203,869

(22) Filed: Jul. 7, 2016

(65) Prior Publication Data

US 2017/0175280 A1    Jun. 22, 2017

Related U.S. Application Data

(63) Continuation of application No. 14/975,913, filed on Dec. 21, 2015.

(51) Int. Cl.
*A61B 5/0478* (2006.01)
*A61N 1/04* (2006.01)
(Continued)

(52) U.S. Cl.
CPC .......... *A61B 5/0478* (2013.01); *A61B 5/0022* (2013.01); *A61B 5/6833* (2013.01);
(Continued)

(58) Field of Classification Search
CPC ................. G01R 3/00; Y10T 29/49204; Y10T 29/49222; Y10T 29/49147
See application file for complete search history.

(56) References Cited

U.S. PATENT DOCUMENTS

| 4,409,983 A | 10/1983 | Albert |
| 7,363,705 B2 * | 4/2008 | Kim ......................... G01R 3/00 |
| | | 174/261 |

(Continued)

FOREIGN PATENT DOCUMENTS

WO    2013165474 A1    11/2013

OTHER PUBLICATIONS

Pang et al., "Highly Skin-Conformal Michrohairy Sensor for Pulse Signal Amplification", Advanced Materials, 2014, DOI:10.1002/adm.201403807.

(Continued)

*Primary Examiner* — Livius R. Cazan
(74) *Attorney, Agent, or Firm* — Harrington & Smith

(57) ABSTRACT

An apparatus includes a substrate mechanically and electrically connected on one side of the substrate to multiple metallic probes in one or more arrays and includes the multiple metallic probes in the one or more arrays. In a method, multiple pits may be formed in an array on a first substrate. The pits have a pyramidal shape. A release layer is formed on the first substrate and covers surfaces of the pits. Probe tips are formed in the pits on the first substrate. The probe tips are formed from rigid conductive material. Multiple pillars are formed from rigid conductive material. The pillars are electrically and mechanically connected to a second substrate and to the probe tips. Release is caused of the probe tips from the first substrate, wherein the pillars and probe tips are connected to the second substrate and together form an array of rigid and conductive probes.

6 Claims, 12 Drawing Sheets

(51) Int. Cl.
  *A61N 1/05*       (2006.01)
  *G16H 40/67*      (2018.01)
  *G01R 3/00*       (2006.01)
  *A61B 5/00*       (2006.01)
  *A61B 5/0408*         (2006.01)
  *C25D 1/00*           (2006.01)

(52) U.S. Cl.
  CPC .......... *A61B 5/6839* (2013.01); *A61N 1/0492* (2013.01); *A61N 1/0502* (2013.01); *G01R 3/00* (2013.01); *G16H 40/67* (2018.01); *A61B 5/0408* (2013.01); *A61B 2562/028* (2013.01); *A61B 2562/0215* (2017.08); *A61B 2562/125* (2013.01); *C25D 1/003* (2013.01)

(56) References Cited

U.S. PATENT DOCUMENTS

| | | |
|---|---|---|
| 8,097,926 B2 | 1/2012 | De Graff |
| 8,374,688 B2 | 2/2013 | Libbus et al. |
| 9,173,583 B2 | 11/2015 | Chen et al. |
| 9,200,883 B2 | 12/2015 | Andry et al. |
| 2009/0182393 A1 | 7/2009 | Bachinski |
| 2012/0279287 A1 | 11/2012 | Andry et al. |
| 2014/0275911 A1 | 9/2014 | Chen |
| 2015/0137345 A1 | 5/2015 | Choi et al. |

OTHER PUBLICATIONS

Choong et al., "Highly Stretchable Resistive Pressure Sensors Using a Conductive Elastomeric Composite on a Micropyramid Array", Advanced Materials, 2014 DOI: 10.1002/adma.201305182 pp. 3451-3458.

Chi et al., "Dry-Contact and Noncontact Biopotential Electrodes: Methodological Review", IEEE Reviews in Biomedical Engineering, vol. 3, 2010.

Shyamkumar et al,, "Wearable Wireless Cardiovascular Monitoring Using Textile-Based Nanosensor and Nonomaterial Systems", Electronics 2014, ISSN 2079-020, 3, 504-520; doi: 10.3390/electronics3030504.

Mannsfeld et al., "Highly Sensitivie Flexible Pressure Sensors With Microstructured Rubber Dielectric Layers", Nature Materials, Published online Sep. 12, 2010, DOI: 10.1038/NMAT2834.

Tee et al., "Tunable Flexible Pressure for Sensors Using Microstructured Elastomer Geometries for Intuitive Electronics", Materials Views, Advanced Functional Materials, 2014, 24. pp. 5427-5434.

Rai et al., "Nanotextile Bio-Sensors for Mobile Wireless Wearable Health Monitoring of Neurological and Cardiovascular Disorders", Institute of Smart Structures and Systems (ISSS), J. ISSS vol. 3, No. 1, pp. 27-77, Mar. 2014.

Zang et al., "Advances of Flexible Pressure Sensors Toward Artificial Intelligence and Health Care Application", Royal Society of Chemistry, Materials Horizons, vol. 2, No. 2, Mar. 2014, pp. 133-254.

\* cited by examiner

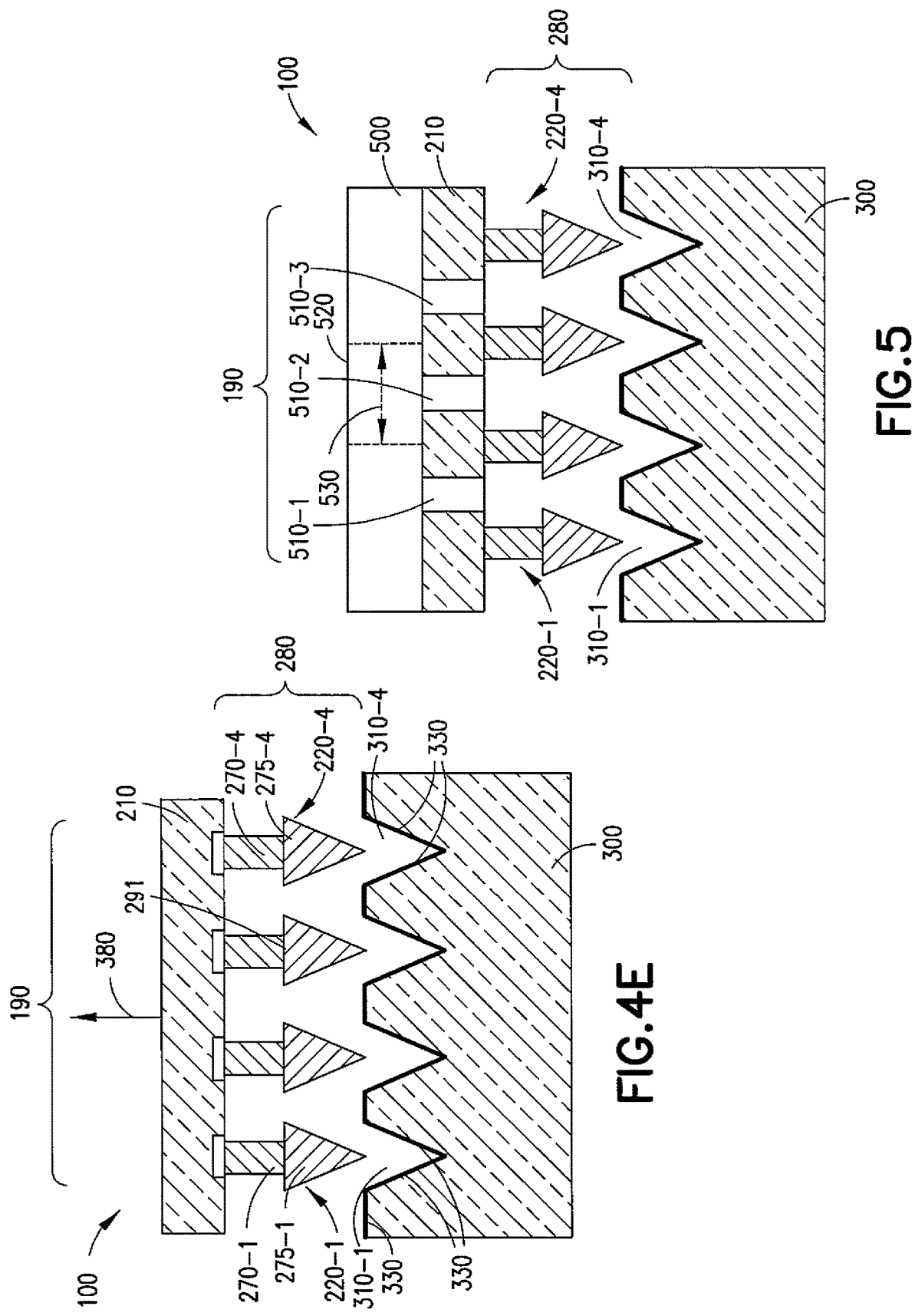

TRANSDERMAL SENSING PROBES AND SMART PATCH SYSTEMS USING SAME

CROSS-REFERENCE TO RELATED APPLICATIONS

This application is a continuation application of U.S. patent application Ser. No. 14/975,913, filed on Dec. 21, 2015, the disclosure of which is hereby incorporated by reference in its entirety.

BACKGROUND

The present invention relates to probes used for bio-sensing, and more particularly to transdermal sensing probes.

This section is intended to provide a background or context to the invention disclosed below. The description herein may include concepts that could be pursued, but are not necessarily ones that have been previously conceived, implemented or described. Therefore, unless otherwise explicitly indicated herein, what is described in this section is not prior art to the description in this application and is not admitted to be prior art by inclusion in this section. Abbreviations that may be found in the specification and/or the drawing figures are defined below, after the detailed description section.

There are a number of probes that are used for bio-sensing. For instance, ECG probes have been implemented in the following: (a) a chest harness; (b) a heart strap, (c) a noncontact vest, (d) a chair; (e) wireless bandages; and (f) a dry chest strap. EEG probes have been implemented in the following: (g) a Neurosky single channel headset; (h) a dry MEMS cap; (i) a fingered dry EEG harness; (j) a dry/noncontact EEG Headband; (k) a dry active electrode; and (l) an ENOBIO wireless dry sensor. See, e.g., Y. Chi, et al. "Dry-Contact And Noncontact Biopotential Electrodes: Methodological Review", IEEE Reviews In Biomedical Engineering, VOL. 3, 2010.

The EEG circuit design, in particular, has been well understood for decades. Dry or non-contact electrodes are desirable for comfort. However, stable contact to skin is a challenge. Also, electrode-skin noise is not well studied.

There are a number of possible improvements in this area. For instance, miniaturization of electrodes could be improved. For EEG circuits, in particular, these tend to be quite large and bulky. Similarly, headset implementations could benefit from miniaturization of the headset. Is it possible to make to make the headset "invisible"? An improvement in electrode-skin contact is desirable, as is an improvement in signal-to-noise ratio.

SUMMARY

This section is intended to include examples and is not intended to be limiting.

In an exemplary embodiment, an apparatus comprises a substrate mechanically and electrically connected on one side of the substrate to a plurality of metallic probes in one or more arrays. The apparatus also comprises the plurality of metallic probes in the one or more arrays.

In another exemplary embodiment, a method comprises forming a plurality of pits in an array on a first substrate, the pits having a pyramidal shape, and forming a release layer on the first substrate and covering surfaces of the plurality of pits. The method also comprises forming in the pits probe tips on the first substrate, the probe tips formed from rigid conductive material; forming a plurality of pillars from rigid conductive material, and electrically and mechanically connecting the plurality of pillars to a second substrate. The method further comprises electrically and mechanically connecting the plurality of pillars to the plurality of probe tips, and causing release of the probe tips from the first substrate, wherein the pillars and probe tips are connected to the second substrate and together form an array of rigid and conductive probes.

BRIEF DESCRIPTION OF THE SEVERAL VIEWS OF THE DRAWINGS

FIG. 3, which includes

FIG. 4, which includes FIGS. 4A through 4E, illustrates another fabrication method for the smart patch in an exemplary embodiment;

FIG. 5 illustrates an example of a breathable and/or heat spreading smart patch, in accordance with exemplary embodiments;

FIG. 8, which includes

DETAILED DESCRIPTION

The word "exemplary" is used herein to mean "serving as an example, instance, or illustration." Any embodiment, described herein as "exemplary" is not necessarily to be construed as preferred or advantageous over other embodiments. All of the embodiments described in this Detailed Description are exemplary embodiments provided to enable persons skilled in the art to make or use the invention and not to limit the scope of the invention which is defined by the claims.

As stated above, there are a number of possible improvements in this area. The instant exemplary embodiments provide some or all of these improvements. For instance, electrodes using the instant probes are further miniaturized, relative to conventional probes. In particular, headset implementations may be further miniaturized relative to conventional implementations, such that it is possible to make to make the headset almost "invisible". Exemplary embodiments provide, relative to conventional probes, an improvement in electrode-skin contact and/or an improvement in signal-to-noise ratio.

The exemplary embodiments concern transdermal sensing probes. Such probes may have a set of relatively inflexible probes in a probe array. The probes in the array may have an anchor structure, which helps to provide a secured contact between the probes and skin, hair, fabric, or other materials.

An overview is first presented, and then additional detail regarding additional exemplary embodiments is presented.

Figure 1:
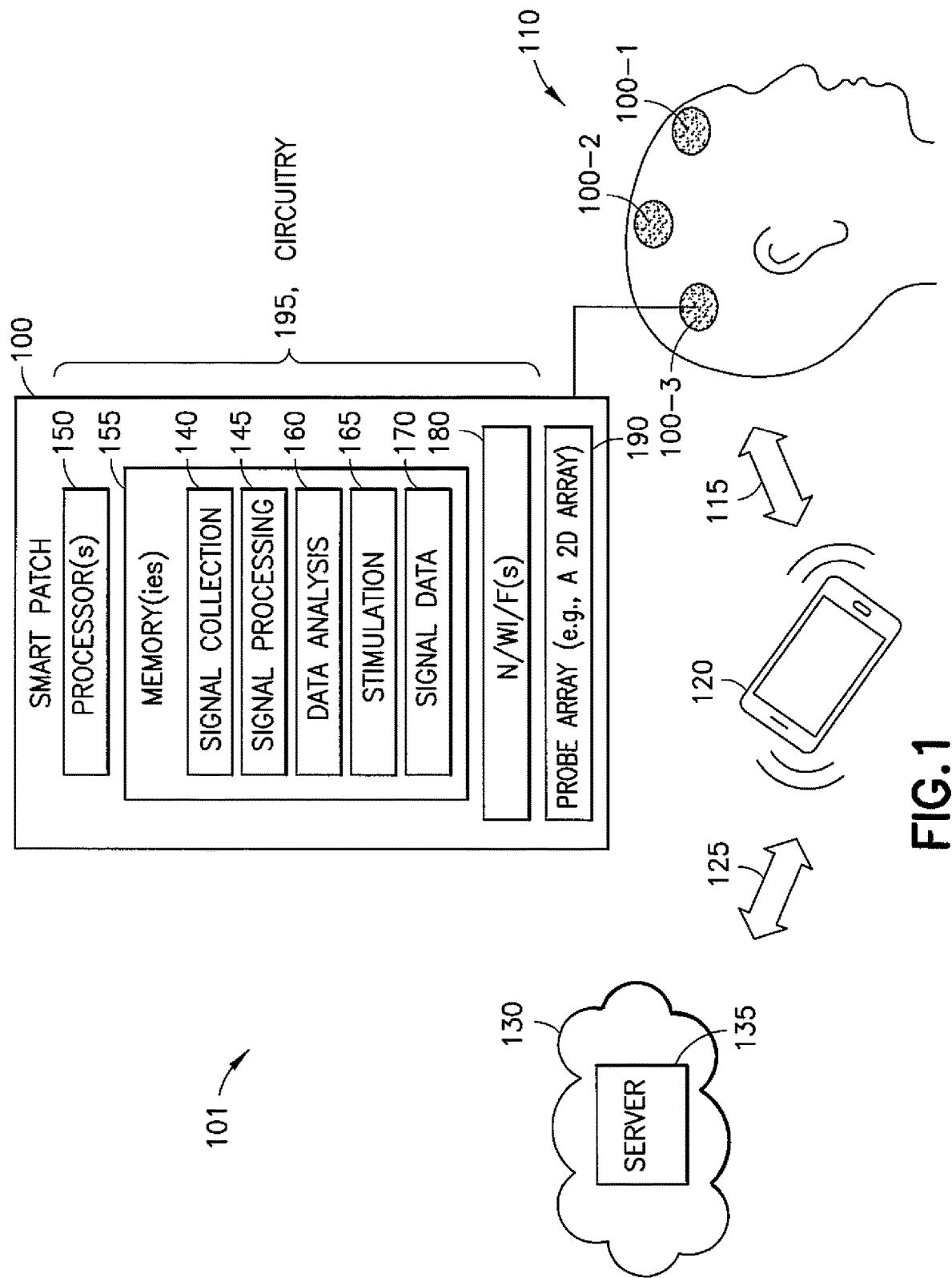
FIG. 1 illustrates an exemplary system for collecting, analyzing, and/or transmitting bio-sensed data using smart patches in an exemplary embodiment.

FIG. 1 is used as part of the overview and illustrates an exemplary system 101 for collecting, analyzing, and/or transmitting bio-sensed data using smart patches 100 in an exemplary embodiment. In this example, there are three smart patches 100-1, 100-2, and 100-3, which are placed proximate or touching a human being's head 110. The three smart patches 100 may be placed on the skin (not shown in FIG. 1), in the hair (not shown), or on fabric (not shown). For this example, the smart patches 100 are being used for EEG signals or other bio-electrical signals, and/or for stimulation.

A single smart patch 100 is shown in block diagram form, and it is assumed that each of the smart patches 100-1, 100-2, and 100-3 is similar, though need not be. The smart patch 100 comprises one or more processors 150, one or more memories 155, one or more network interfaces 180, and a probe array 190, which may be a two-dimensional (2D) probe array (note that one single dimension arrays are illustrated in following figures). The one or more memories 155 comprise signal collection module 140, signal processing module 145, data analysis module 160, stimulation module 165, and signal data 170. Signal data 170 in one example is EEG signal data from the probe array 190. The signal collection module 140 controls the probe array 190 and collects the signal data 190 at least in part. The signal processing module 145 performs and/or controls signal processing, such as analog to digital conversion. The data analysis module 160 performs and/or controls data analysis, such as determining starting points and ending points for waveforms, and/or abnormal electrical signals such as for seizures or convulsions. The stimulation module 165 performs and/or controls stimulation, such as acupuncture or electrical stimulation. The one or more processors 150, one or more memories 155, and one or more N/W I/Fs 180 are circuitry 195.

The one or more network (N/W) interfaces (I/Fs) 180 may be hardwired or wireless, and may operate over a number of different networks, such as serial networks (e.g., USB, universal serial bus), local area networks (such as Bluetooth or Wi-Fi), optical networks, or the like, as examples.

In an exemplary embodiment, the smart patches 100 wirelessly transmit, via a wireless link 115, information to the remote, wireless, movable device 120, shown in this example as a smartphone. The device 120 could also be a tablet, personal computer, and the like. The device 120 wirelessly transmits, via a wireless link 125, the same or different information to the network 130 (e.g., the Internet) and to the server 135.

In one exemplary embodiment, the modules 140, 145, 160, and 165 are implemented in part or completely as computer-readable code that, when executed by the one or more processors 150, causes the smart patch to collect, analyze, and/or transmit bio-sensed data. In another exemplary embodiment, the modules 140, 145, 160, and 165 are implemented in part or completely as circuitry 195 that causes the smart patch to collect, analyze, and/or transmit bio-sensed data. In other examples, there are no processor(s) 150 or memory/memories 155, and the modules 140, 145, 160, and 165 are implemented as discrete circuitry 195, which may have their own memory or the smart patch may have its own memory 155, which could be shared by the modules 140, 145, 160, and 165, or both.

The modules 140, 145, 160, and 165, the memory/memories 155, the processor(s) 150, and the N/W IF(s) 180 can be built internal to a substrate (shown, e.g., in FIG. 2) and/or external to the substrate and attached to the substrate (e.g., as an integrated circuit). If discrete components are used, there could be one or multiple discrete components.

There are many different ways to configure a system 101. For instance, there may be more or fewer modules 140, 145, 160, and 165. As an example, the smart patch 100 may be used solely for stimulation and none of the other modules 140, 145, 160, and data 170 could be used (and the NW IF(s) 180 might also not be used, depending on implementation). Even for stimulation, however, the modules 140, 145, 160 and the data 170 could be used, e.g., to determine the stimulation that is being applied to the probe array 190 under control of the stimulation module 165. If there is no stimulation to be performed by the probe array 190, then the stimulation module 165 would not be used. As a further example, the smart patch 100 may be only a signal collection tool, such that only the signal collection module 140 and the signal processing module 145 would be used to create the signal data 170, and the signal collection module 140 would control the N/W I/F 180 to transmit the data 170. The server 135 could perform some of the data analysis 160 in this example. The server 135 could additionally or instead provide access to the signal data 170, e.g., by the human 110 or a doctor. Still other examples are possible.

Figure 2:
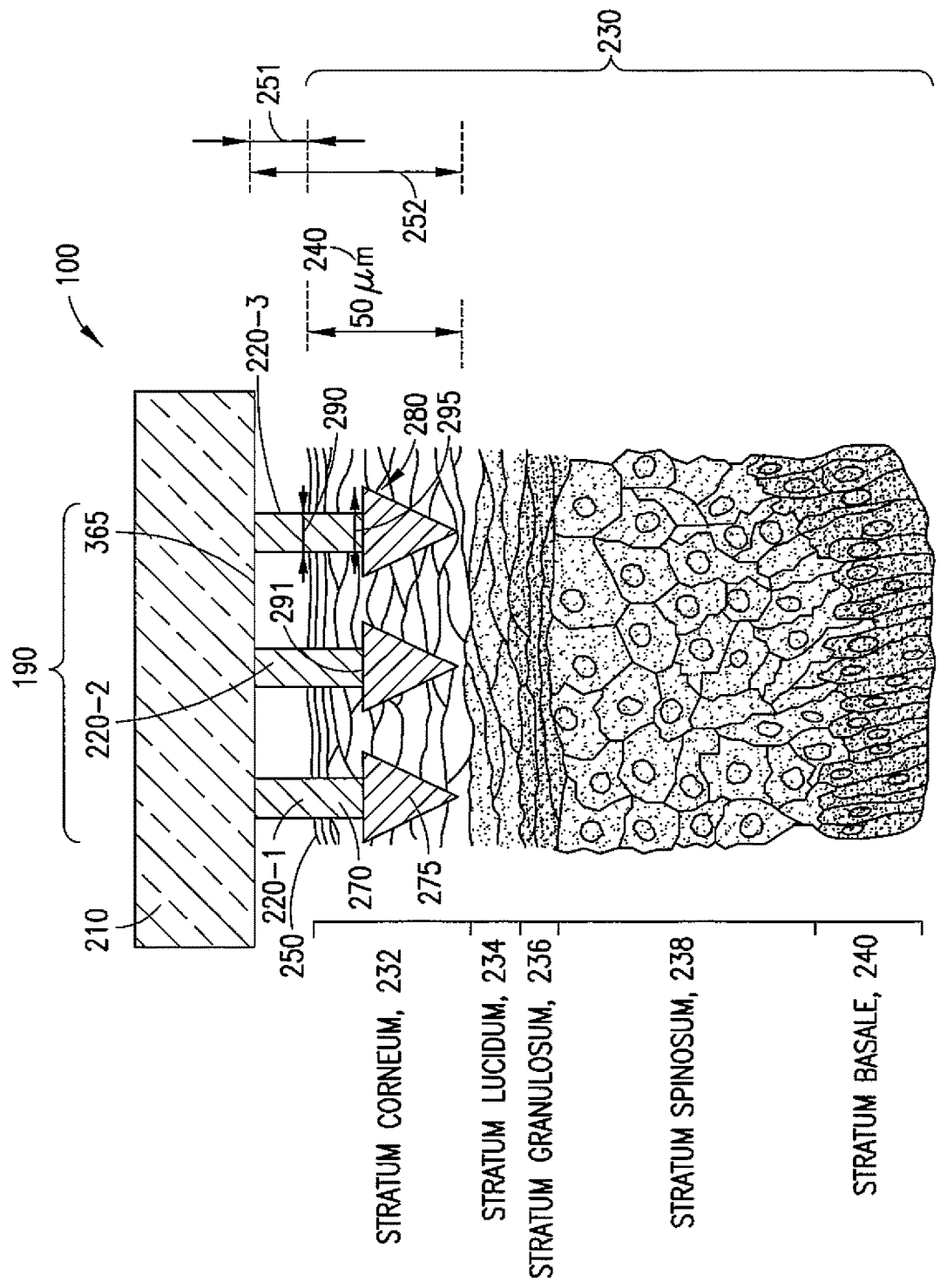
FIG. 2 is an example of a smart patch with transdermal sensing probes being used on human skin.

FIG. 2 shows a smart patch 100 attached to a portion of skin 230. The skin 230 includes the stratum corneum 232, the stratum lucidum 234, the stratum granulosum 236, the stratum spinosum 238, and the stratum basale 240. The substrate 210 of the smart patch 100 is attached to the probe array 190, illustrated by three probes 220-1, 220-2, and 220-3. The probes 220 are transdermal, meaning that the probes 220 enter through and into at least part of the epidermis (e.g., illustrated at least by the stratum corneum 232). In this example, the probes 220 enter 50 μm into the skin 230 from the surface 250 of the skin 230. Each probe 220 comprises a pillar 270 and a tip 275, which together form an anchor structure 280. It is expected that this distance 240 should not cause pain, but should provide a secure contact and lower impedance for human body electrical activity sensing or as a stimulation interface. Additionally, the height 252 of each probe is controlled for less intrusiveness. The anchor structure 280 also helps to provide a secure contact, as the tip 275 in this example is shaped like a pyramid and the pillar 270 is shaped like a cylinder, where the width 290 of the cylinder is smaller than the width 295 of the base (opposite the vertex) of the cone at a junction 291 between the pillar 270 and the tip 275. As examples, the width of pillar could be on the order of ~50 μm and the height might be greater than 100 μm. The thickness of region 251 could be less than 50 μm. Overall size of substrate can be variable from 1 mm to 100 mm. The region 251 between the surface 250 of the skin 230 and a "bottom" surface 365 of the substrate 210 may be completely or partially filled with a material such as an adhesive or a gel. The material may help with adhesion between the smart patch 100 and the skin 230.

The probes 220 are different from probes such as those formed using polymer films (e.g., PDMS), as each probe made with a polymer films is flexible, whereas each probe 220 is inflexible. In particular, the probes used herein are rigid metallic or alloy probes because they are formed based on, e.g., electrolytic plating. Therefore, they are electrically conductive in comparison to probes such as those made from polymer films. If the substrate 210 is inflexible, then the entire smart patch 100 will be inflexible. If the substrate 210 is flexible, this will impart some amount of flexibility between the probes 220, but each probe 220 is still inflexible.

The probe array 190 and the smart patch 100 may provide transferrable bio-sensing/stimulating probe arrays. That is, the probe array 190 may be used on many different substrates 210, including flexible and inflexible substrates. The anchor-shaped probe tips 275, creating the anchor structure 280, are useful for a transdermal application. Other examples are possible, and one such example is shown in FIG. 8. In particular, the patch 100 is "self-sticking" on skin and always in contact. Furthermore, since the probes 220 are inflexible, they are less susceptible to lateral displacement. Additionally, the probe arrays 190 adhere to a fabric surface and many other surfaces with ease.

Now that an introduction has been presented, more detailed examples are presented. The detailed examples start with some exemplary techniques for probe creation and transfer to a substrate.

Figure 3A:
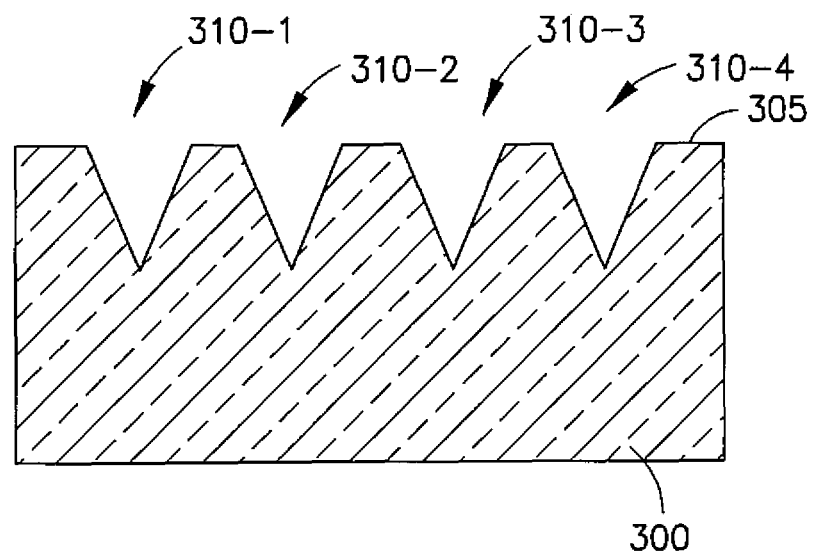
FIGS. 3A through 3F, illustrates a fabrication method for a smart patch in an exemplary embodiment.

Turning to FIG. 3, which includes FIGS. 3A through 3F, this figure illustrates a fabrication method for a smart patch in an exemplary embodiment. Additional examples of the processing that may occur for FIGS. 3A, 3B, and 3C may also be found in U.S. Publication No. 2012/0279287, by Paul Andry, Bing Dang, and Steven Wright, entitled "Transferable Probe Tips", filed on May 5, 2011, and assigned to International Business Machines Corporation. The fabrication method starts in FIG. 3A, which illustrates a molding etching process. In FIG. 3A, the substrate 300, which may be for instance a silicon substrate having a <100> orientation, has been etched (e.g., through anisotropic etching) to form pits 310, of which pits 310-1 through 310-4 are shown. In U.S. Publication No. 2012/0279287, a hardmask layer is used to form the pits 310, and such a technique may be used herein. This technique (and the hardmask layer) is not shown here. In fact, FIG. 3A shows the substrate 300 after the hardmask layer has already been removed. The pits 310 are of an inverse pyramidal shape in this example, but are not limited to this shape. The substrate 300 has a surface 305. The anisotropic Si etch may use, for example, tetramethylammonium hydroxide (TMAH). Silicon anisotropic etchants have etch rates along (111) directions of the crystal lattice which are much slower than the etching that occurs in other directions.

Figure 3B:
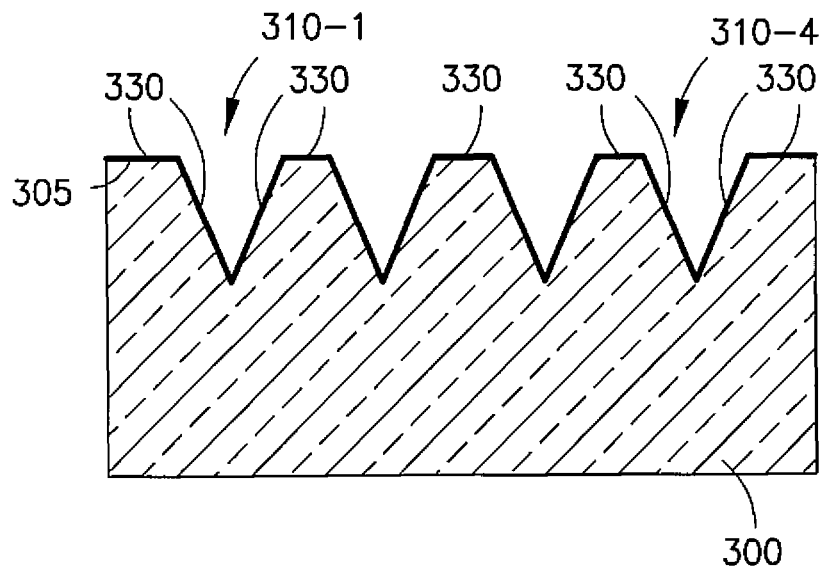

FIG. 3B illustrates a result after a seed layer 330 has been formed on the surface 305 of the substrate 300. The seed layer 330 helps with, e.g., subsequent plating (FIG. 3C) and also release (FIG. 3F). The seed layer 330 may also be referred to as a delamination layer and be a low-adhesion or sacrificial layer.

Figure 3C:
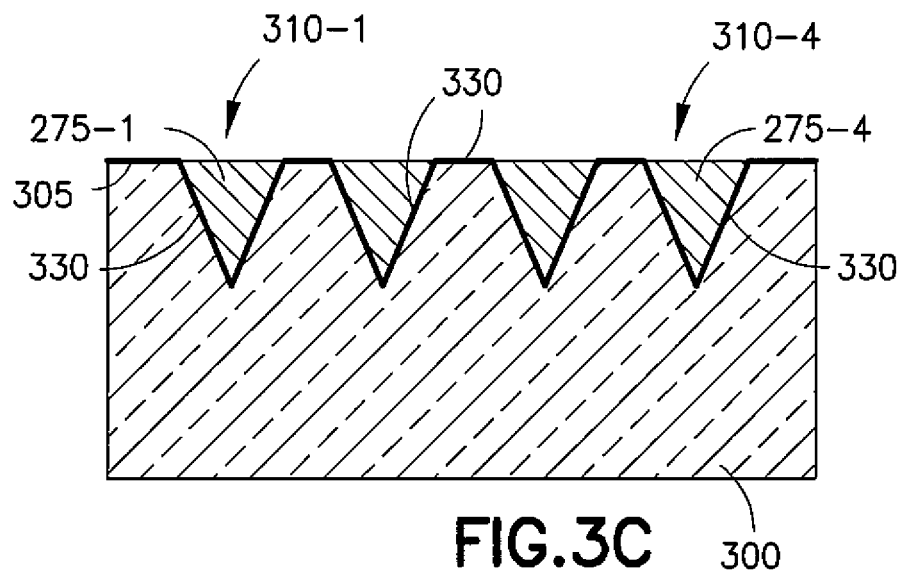
Figure 3D:
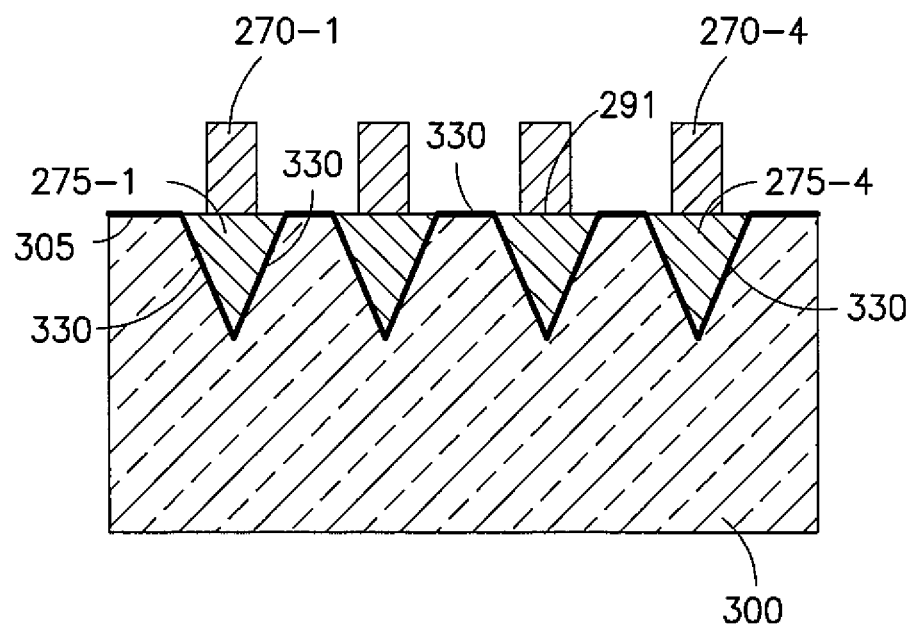

FIG. 3C shows a result after a layer of metal has been formed on the surface of the substrate and subsequently removed, e.g., using CMP. The result forms metal tips 275, of which tips 275-1 through 275-4 are shown. FIG. 3D illustrates a result after a second metal layer has been formed on the surface 305 of the substrate 300 and pillars 270 (of which pillars 270-1 through 270-4 are shown) have been formed using lithographic and etching techniques. The metal in the pillars 270 is similar to or the same as the metal in the tips 275. Pillars 270 are plated directly over the tips 275 through a subsequent plating step. Since the pillars 270 are the same metal or alloy (such as Cu), the pillars 270 and the tips 275 are intimately connected at the junction 291 between the pillars 270 and the tips 275.

Figure 3E:
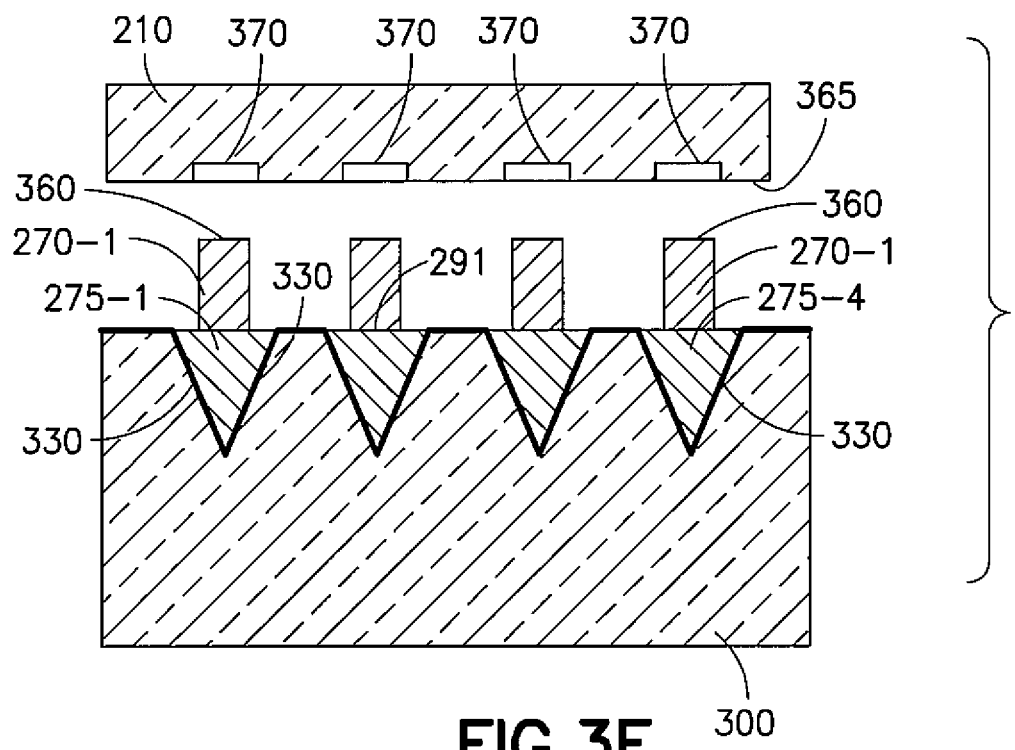
Figure 3F:
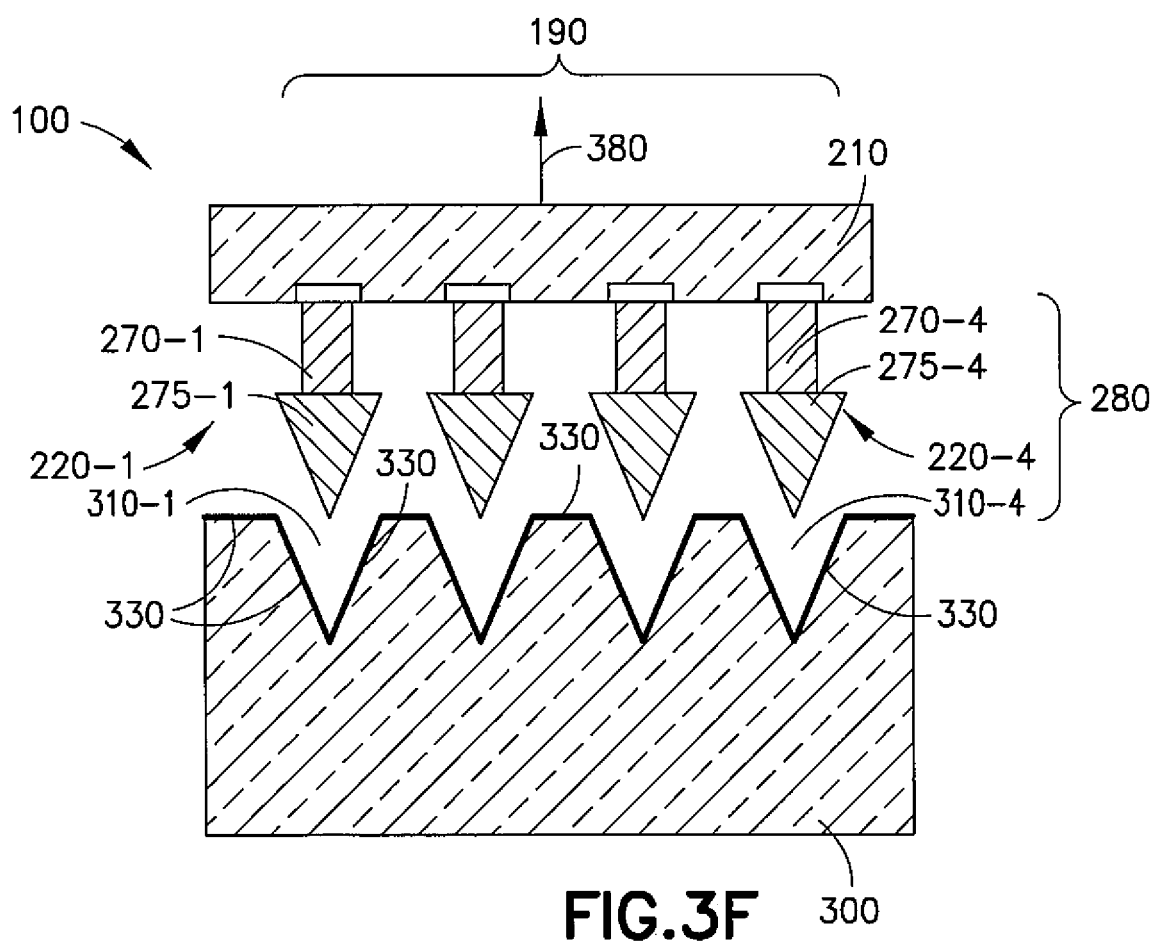

Referring to FIG. 3E, this figure illustrates a substrate 210 that is about to be placed on and connected to the "top" surfaces 360 of the pillars 270. The "bottom" surface 365 of the substrate 210 mates with the top surfaces 360 at predetermined locations 370 (such as at pads) on the substrate, e.g., where electrical and physical connections may be made between the substrate 210 and the pillars 270. As examples, a solder layer or conductive adhesive may be used to bond the substrate 210 and the pillars 280. Subsequent to the attachment of the substrate to the pillars 270, FIG. 3F illustrates a release step, where the substrate 210 and probe array 190 are pulled away (illustrated by reference 380) from the substrate 300. The probe array 190 (each probe 220 comprising a pillar 270 and a tip 275, and each probe 220 has an anchor structure 280) is therefore transferred to the substrate 210. The U.S. Publication No. 2012/0279287 describes transferable probe tips, and the techniques described there may also be used herein. The seed layer 330 still remains on the substrate 300 after release because of controlled low adhesion. The separation can be a mechanical peeling or pulling with vacuum chucks, as examples.

The substrate 210 may be flexible or inflexible. A flexible substrate can be anything active/passive suitable for wearing on a human body, such as a polymer-based flexible circuit, a thin semiconductor, a flexible electronic system, and the like. Inflexible substrates 210 may be rigid multi-layer printed circuit boards, Si, ceramic, or glass based integrated circuits, and the like.

Figure 4A:
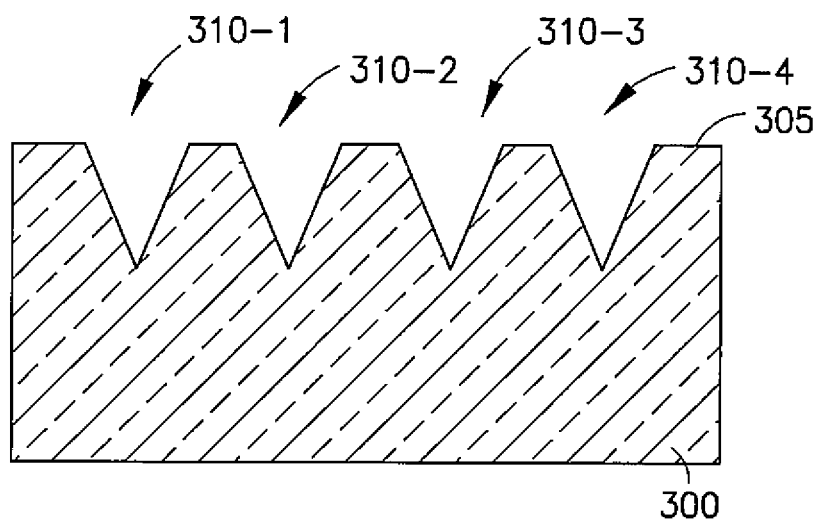
Figure 4B:
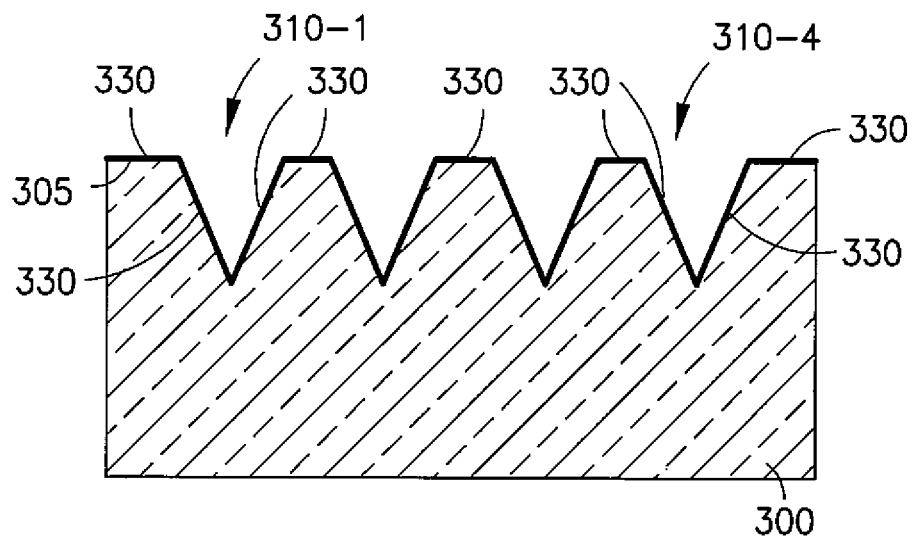
Figure 4C:
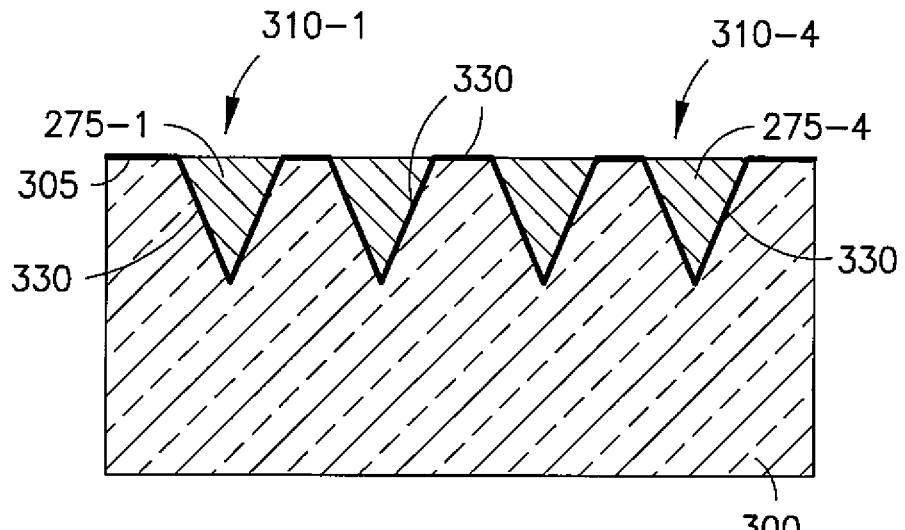

Turning to FIG. 4, which includes FIGS. 4A through 4E, this figure illustrates another fabrication method for a smart patch in an exemplary embodiment. Additional examples of the processing that may occur for FIGS. 4A, 4B, and 4C may also be found in U.S. Publication No. 2012/0279287, by Paul Andry, Bing Dang, and Steven Wright, entitled "Transferable Probe Tips", filed on May 5, 2011, and assigned to International Business Machines Corporation. FIGS. 4A, 4B, and 4C are equivalent to FIGS. 3A, 3B, and 3C, respectively.

Figure 4D:
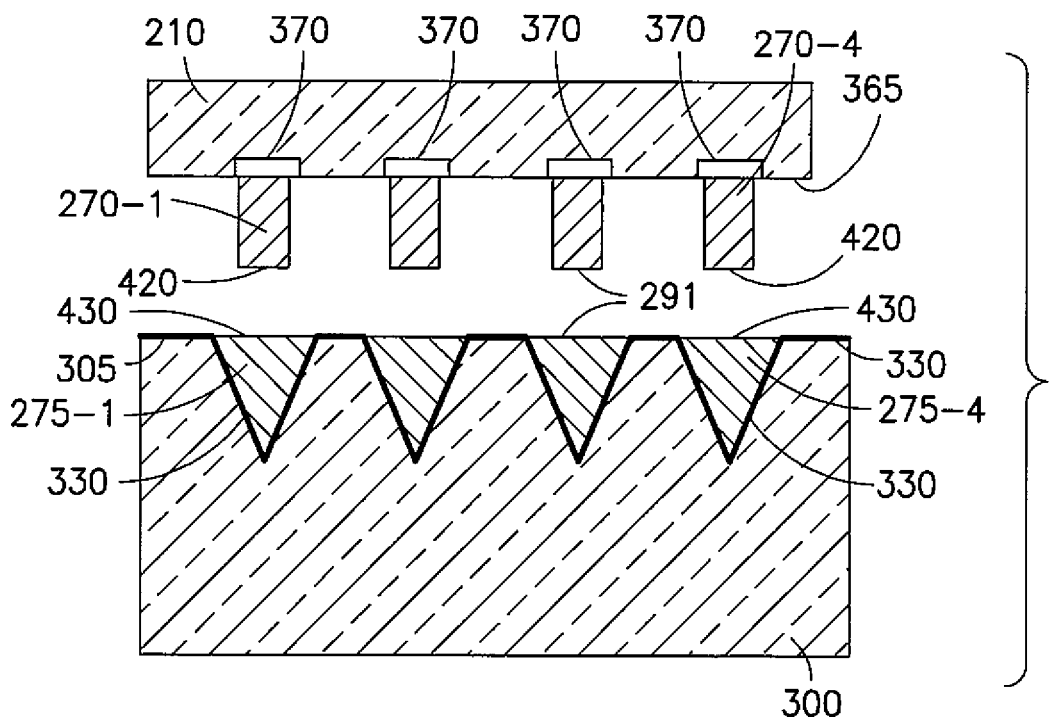

In FIG. 4D, this figure illustrates that the pillars 270 may be mechanically and electrically connected to the substrate 210 (e.g., at predetermined locations 370) (at the junctions 291) prior to the pillars being mechanically and electrically connected to the tips 275. That is, the pillars 270 are physically attached to the substrate 210 (and subsequently to the tips 275). For instance, the pillars 270 may be formed on the substrate using lithography and electrolytic plating techniques. More particularly, dry film photoresist may be laminated on (e.g., flexible) substrate 210. After mask exposure and development of the dry film photoresist, the pillars 270 can be formed by electroplating. As with FIG. 3, the pillars 270 are formed of one or more metals similar to or the same as the one or more metals in the tips 275.

FIG. 4E shows a smart patch 100 after the pillars 270 are mechanically and electrically connected to the tips 275, and after the tips 275 have been released from the substrate 300 (as indicated by reference 380). The mechanical and electrical connections (e.g., at junctions 291) may be made using many different techniques. For instance, solder alloy such as Sn and In may be used for bonding. Other materials such as conductive Ag epoxy may also be used to connect the tips. After release, the probes 220 are formed, each having an anchor shape 280.

Additional examples are presented in FIGS. 5-8.

Referring to FIG. 5, this figure illustrates an example of a breathable and/or heat spreading smart patch 100, in accordance with exemplary embodiments. After release of the tips 275 from the pits 310, the probes 220 are formed, each having an anchor shape 280. In this example, there are a number of vias 510, of which vias 510-1, 510-2, and 510-3 are shown. The vias 510 can be metallized for electrical function or just be mechanical vias (for instance, openings that are not metalized and left unfilled or filled with breathable material) for ventilation. In this example, the material 500 may be a breathable material.

In another example, the vias 510 and optional heat spreader 500 (e.g., a heat-conducting fabric) could be used to transfer heat from the skin 230. As another example, these concepts are combined, such that a heat spreader 500 is used with an aligned pattern of the vias 510 to allow ventilation. In an example, the heat spreader 500 covers vias 515 used for heat spreading but does not cover the vias 515 used for ventilation. For instance, in region 530, the reference 520 indicates in one example there is no material 500. In another example, the region 530 could be filled with a breathable material 520. It may also be possible to use a heat spreading material that also is breathable, where the material 500 would then cover all of the vias 510. These techniques could allow the smart patch 100 to breathe and dissipate heat for extra comfort.

Figure 6:
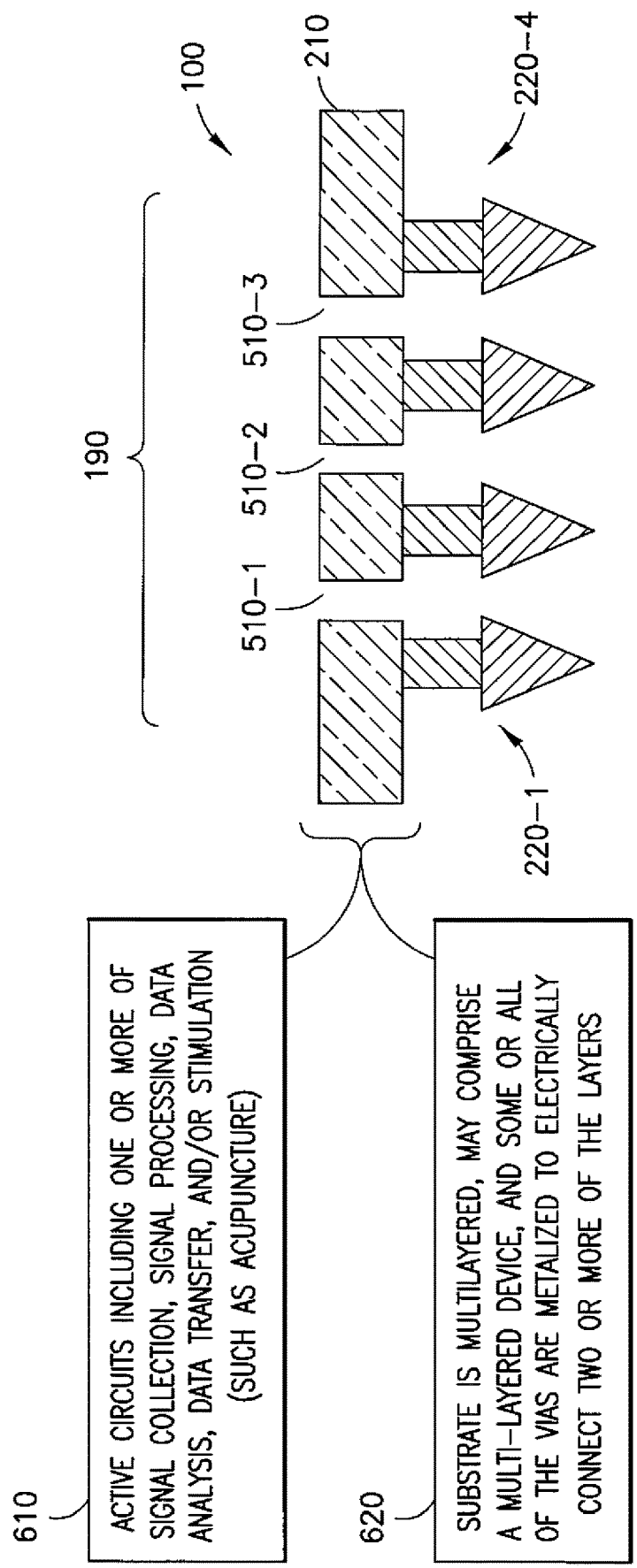
FIG. 6 illustrates an example of a smart patch with active circuits in the substrate, in accordance with exemplary embodiments.

Turning to FIG. 6, this figure illustrates an example of a smart patch 100 with active circuits in the substrate, in accordance with exemplary embodiments. FIG. 6 illustrates that the substrate 210 is configured (reference 610) to have active circuits (e.g., some or all of circuitry 195) with one or more of signal collection 140, signal processing 145, data analysis 160, data transfer (e.g., via N/W I/F(s) 180), and/or stimulation 165 (such as acupuncture or electrical stimulation). Regarding acupuncture, this may not apply to traditional acupuncture because the anchor structures 280 and acupuncture needles are different. Traditional acupuncture uses a single needle at a critical point and the needles are much longer to penetrate through a deeper region. However, this invention may apply to the electro acupuncture, in which pairs of needles are used to pass continuous electric pulses using small clips. These devices are used to adjust the frequency and intensity of the impulse being delivered, depending on the condition being treated. This example also shows vias 510, which in this case might be metalized (see reference 620). The substrate 210 can therefore be a multi-layered substrate forming a multi-layered device formed using semiconductor processing techniques. See reference 620. The substrate 210 may therefore be an ultra-thin, ultra-small chip if desired. For instance, a thickness could be less than 50 µm for the substrate 210 with a chip size less than 1 mm×1 mm. Of course, other sizes are possible.

Figure 7:
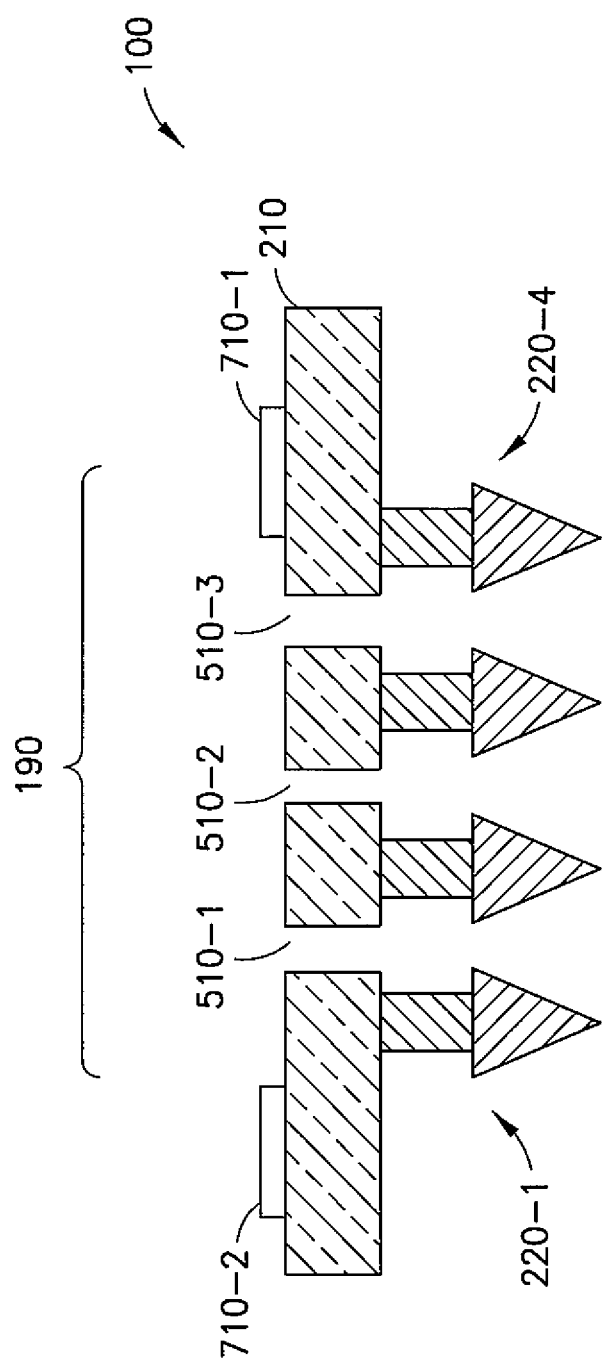
FIG. 7 illustrates an example of a smart patch with elements attached to the substrate, in accordance with exemplary embodiments.

FIG. 7 illustrates an example of a smart patch 100 with elements 710 attached to the substrate, in accordance with exemplary embodiments. The elements 710 may be an alternative to the active circuits in the substrate as in FIG. 6 or may be used with the active circuits in the substrate in FIG. 6. The vias 510 are shown, which as with FIG. 6 may be metalized. The substrate 210 further comprises two elements 710-1 and 710-2, each of which is mechanically and electrically connected to the substrate 210. Each element may be an integrated circuit, MEMS, an optical element or a group of optical elements, an antenna, a heat spreader, an energy scavenging unit, a battery, and/or a capacitor, and the like. Energy scavenging may involve one or more piezoelectric materials or other materials that can be used to generate electricity, which can then be used to charge materials such as a supercapacitor or battery, for instance. The elements 710-1 and 710-2 can also perform the functionality in circuitry 195 of FIG. 1 or the reference 610 of FIG. 6.

Figure 8A:
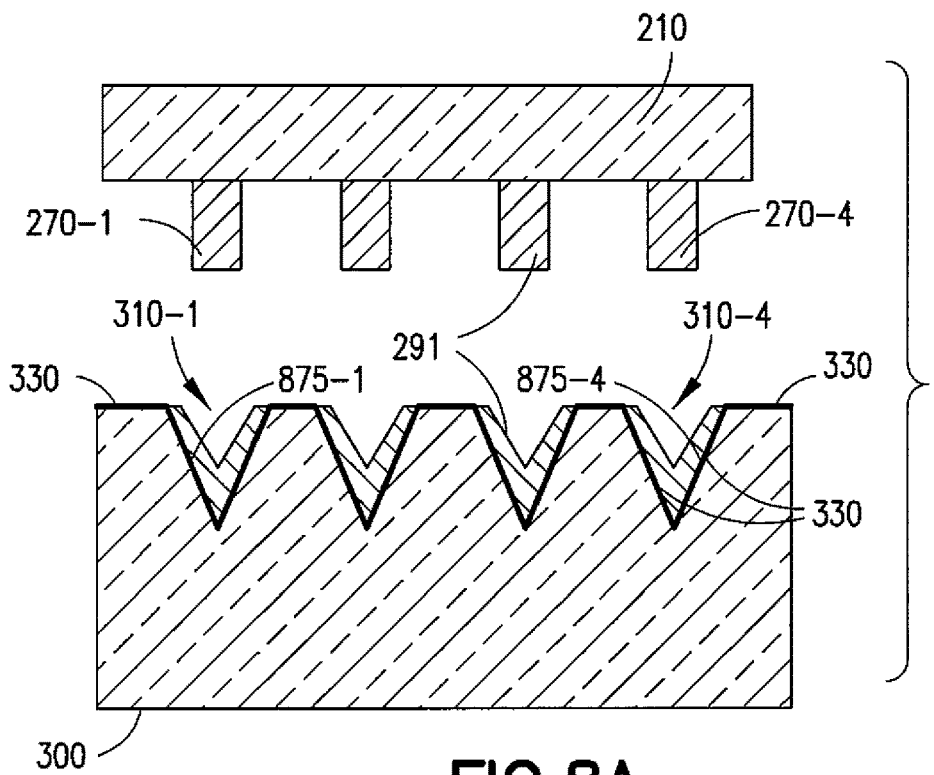
FIGS. 8A and 8B, illustrates another fabrication method for the smart patch in an exemplary embodiment.
Figure 8B:
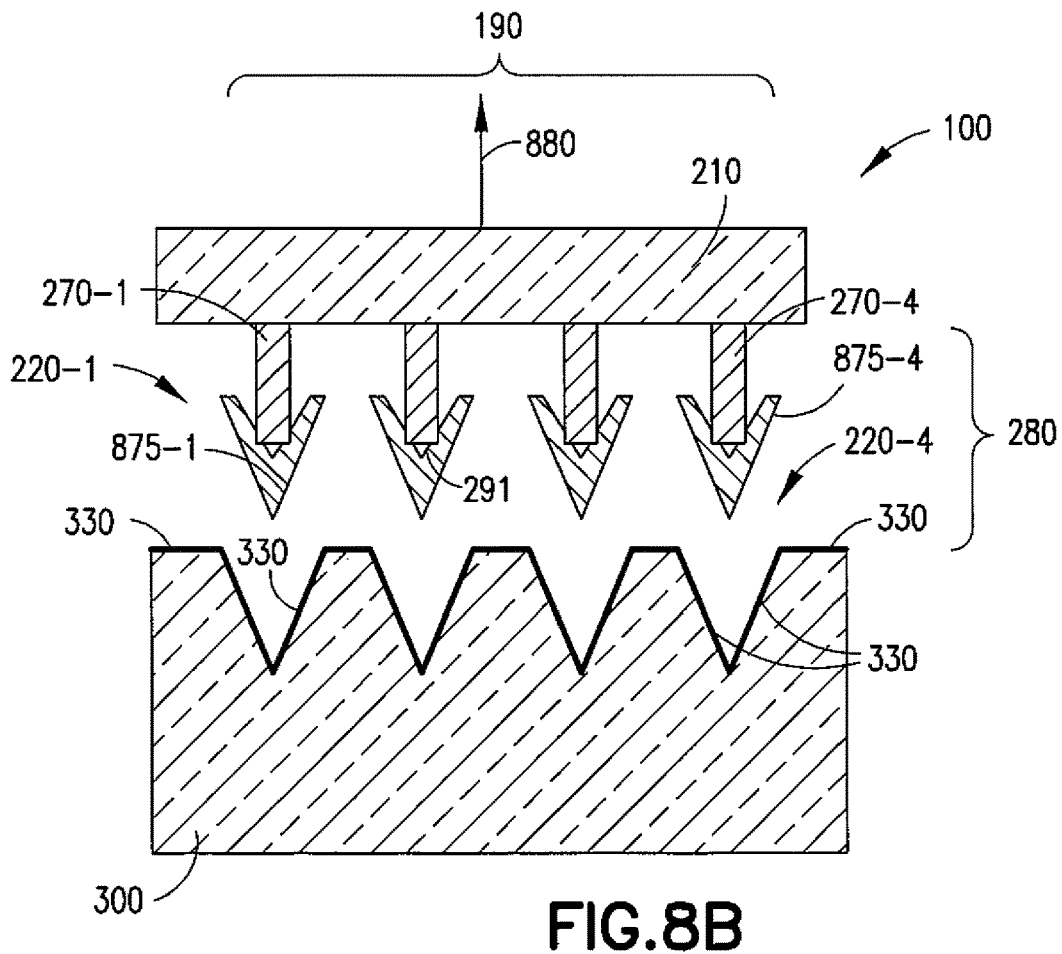

Turning to FIG. 8, this figure, which includes FIGS. 8A and 8B, illustrates another fabrication method for the smart patch 100 in an exemplary embodiment. In this example, the pits 310, of which pits 310-1 through 310-4 are shown, are partially filled pits (see FIG. 8A) that can then form anchor shaped tips 875 (of which tips 875-1 through 875-4 are shown). After release (indicated by reference 880 in FIG. 8B), the probes 220 are formed, each comprising a pillar 270 and a tip 875. Additionally, each probe 220 has an anchor structure 280. The tips 875 have an arrow shape due to the partially formed pits. The mechanical and electrical connections (e.g., at junctions 291) may be made using many different techniques. For instance, solder alloy such as Sn and In may be used for bonding. Other materials such as conductive Ag epoxy may also be used to connect the tips. After release, the probes 220 are formed, each having an anchor shape 280.

As described herein, one or more embodiments of the embodiments can include one of multiple ways to remove a structure on top of a seed layer 330 (also called a delamination layer), which may be a low-adhesion or sacrificial layer: 1) rely on a very low-adhesion layer, which allows the structure to be peeled off (e.g., essentially a mechanical delamination process), or 2) provide a layer (for example, a sacrificial layer) that either thermally decomposes or can be chemically dissolved, which also allows delamination.

In one or more embodiments of the invention, a metallic probe 220 can include at least one of nickel (Ni), copper (Cu), tungsten (W), cobalt (Co), titanium (Ti), iron (Fe), tantalum (Ta), tantalum nitride (TaN), platinum (Pt), palladium (Pd), gold (Au), molybdenum (Mo), rhenium (Re), beryllium (Be), and silver (Ag). Also, a seed layer 330 can include at least one of low-temperature silicon dioxide ($SiO_2$), sputtered copper (Cu), sputtered gold (Au), sputtered aluminum (Al), and spin-on polycarbonate. Further, a bonding alloy can include at least one of tin (Sn), gold-tin (AuSn), tin-silver (SnAg), tin-silver-copper (SnAgCu), indium (In), and tin-lead (SnPb).

Note that many or all of the patches above can also adhere to fabric, e.g., for a "smart dust" application. Smart dust is a system of many tiny sensors, robots, or other devices. These may include microelectromechanical systems (MEMS). As described previously, these patches may be placed on skin, in hair, or on fabric as examples.

Figure 9:
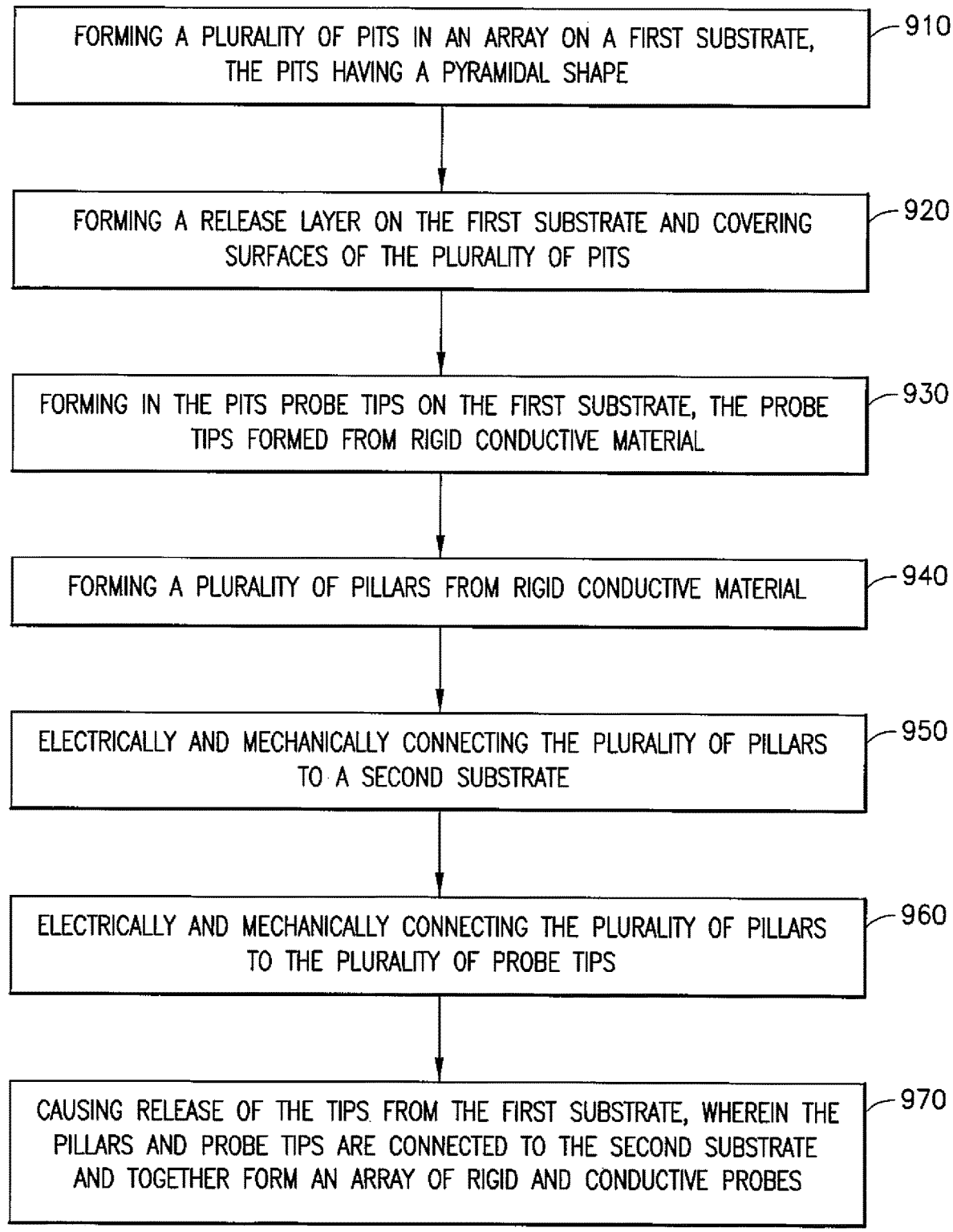
FIG. 9 is a flowchart illustrating a fabrication method for transdermal sensing probes in accordance with an exemplary embodiment.

Turning to FIG. 9, this figure is a flowchart illustrating a fabrication method for transdermal sensing probes in accordance with an exemplary embodiment. FIG. 9 is a restatement of some of the main steps for the methods corresponding to FIGS. 3, 4, 5, 6, 7, and 8. These steps have already been described above, but are restated here for ease of reference.

In block 910, a plurality of pits 310 are formed in an array on a first substrate 300. The pits 320 (see, e.g., FIGS. 3-8) have a pyramidal shape. Block 920 concerns forming a release layer on the first substrate and covering surfaces of the plurality of pits. In block 930, the operation is performed of forming in the pits 10 probe tips 275 on the first substrate 300. The probe tips are formed from rigid conductive material. In block 940, a plurality of pillars 270 are formed from rigid conductive material. In block 950, the plurality of pillars 270 are electrically and mechanically connected to a second substrate 210. Block 960 entails electrically and mechanically connecting the plurality of pillars 270 to the plurality of probe tips 275. Block 970 includes causing release of the probe tips 275 from the first substrate 300, wherein the pillars 270 and probe tips 275 are connected to the second substrate 210 and together form an array 190 of rigid and conductive probes 220.

Another example is the method of FIG. 9, wherein: forming a plurality of pillars from rigid conductive material and electrically and mechanically connecting the plurality of pillars to a second substrate further comprise forming the pillars on corresponding ones of the probe tips, one pillar per probe tip, wherein forming the pillars on corresponding ones of the probe tips also electrically and mechanically connects the plurality of pillars to the second substrate; and electrically and mechanically connecting the plurality of pillars to a second substrate further comprises electrically and mechanically connecting the plurality of pillars to the second substrate using one of a solder layer or a conductive adhesive to bond the second substrate and the plurality of the pillars, wherein electrically and mechanically connecting the plurality of pillars to the second substrate is performed after forming the plurality of pillars.

Another method is the example of the previous paragraph, wherein forming the pillars further comprises forming the pillars using lithographic and etching techniques.

Another example is the method of FIG. 9, wherein: forming a plurality of pillars from rigid conductive material and electrically and mechanically connecting the plurality of pillars to a second substrate further comprise forming the pillars on the second substrate, wherein forming the pillars on the second substrate electrically and mechanically connects the plurality of pillars to the second substrate, wherein forming the pillars on the second substrate occurs before electrically and mechanically connecting the plurality of pillars to the plurality of probe tips; and electrically and mechanically connecting the plurality of pillars to the plurality of probe tips further comprises bonding the plurality of pillars to the plurality of probe tips.

A further example is a method of the previous paragraph, wherein: forming the pillars on the second substrate further comprises forming the pillars on the second substrate using lithography and electrolytic plating techniques; and bonding the plurality of pillars to the plurality of probe tips further comprises one of using a solder alloy for the bonding or using a conductive epoxy for the bonding.

Another example is the method of FIG. 9, wherein: forming in the pits probe tips on the first substrate further comprises forming in the pits the probe tips such that a surface of the probe tips aligns with a surface of the first substrate.

Another example is the method of FIG. 9, wherein: forming in the pits probe tips on the first substrate further comprises forming in the pits the probe tips such that a surface of the probe tips is beneath a surface of the first substrate.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following abbreviations that may be found in the specification and/or the drawing figures are defined as follows:
CMP chemical-mechanical polishing
ECG electrocardiogram (also known as EKG)
EEG electroencephalography
ENOBIO a dry electrophysiology sensor employing nanotechnology
MEMS microelectromechanical systems
PDMS polydimethylsiloxane

What is claimed is:

1. A method, comprising:
forming a plurality of pits in an array on a first substrate, the pits having a pyramidal shape;
forming a release layer on the first substrate and covering surfaces of the plurality of pits;
forming in the pits probe tips on the first substrate, the probe tips formed from rigid conductive material;
forming a plurality of pillars from rigid conductive material, wherein a probe comprises a pillar and a probe tip together forming a transdermal anchor structure;
forming a plurality of pads within a second substrate;
electrically and mechanically connecting the plurality of pillars to the second substrate, wherein a bottom surface of the second substrate mates with top surfaces of the pillars at the pads of the second substrate providing electrical and physical connections between the second substrate and the pillars;
wherein the pads reside within the second substrate and have a surface that is flush with the bottom surface of the second substrate at a point of contact of the top surfaces of the pillars and the bottom surface of the second substrate;
forming a plurality of vias in the second substrate that are unfilled or filled with breathable material;
electrically and mechanically connecting the plurality of pillars to the plurality of probe tips; and
causing release of the probe tips from the first substrate, wherein the pillars and probe tips are connected to the second substrate and together form an array of rigid and conductive probes configured as a transdermal smart patch;
wherein the transdermal smart patch comprises circuitry to sense bio-electrical signals and/or provide stimulation via the array of rigid and conductive probes.

2. The method of claim 1, wherein:
forming a plurality of pillars from rigid conductive material and electrically and mechanically connecting the plurality of pillars to a first substrate further comprise forming the pillars on corresponding ones of the probe tips, one pillar per probe tip, wherein forming the pillars on corresponding ones of the probe tips also electrically and mechanically connects the plurality of pillars to the first substrate; and
electrically and mechanically connecting the plurality of pillars to the second substrate further comprises electrically and mechanically connecting the plurality of pillars to the second substrate using one of a solder layer or a conductive adhesive to bond the second substrate and the plurality of the pillars, wherein electrically and mechanically connecting the plurality of pillars to the second substrate is performed after forming the plurality of pillars.

3. The method of claim 2, wherein forming the pillars further comprises forming the pillars using lithographic and etching techniques.

4. The method of claim 1, wherein forming in the pits probe tips on the first substrate further comprises forming in the pits the probe tips such that a surface of the probe tips aligns with a surface of the first substrate.

5. The method of claim 1:
wherein the probe tips comprise a vertex and a base;
wherein a junction where one of the plurality of pillars meets a probe tip is at the base;
wherein the width of the base is larger than the width of the pillar at the junction to form the transdermal anchor structure; and
wherein the probe tip comprises a recess within the base such that the junction is within the recess.

6. The method of claim 1, further comprising:
collecting the bio-electrical signals from the plurality of probes;
transmitting data corresponding to the signals to a remote device over one or more network interfaces;
wherein the remote device wirelessly transmits, via a wireless link, data corresponding to the signals to a server within a network;
wherein the server is configured to i) perform analysis of the data corresponding to the signals received from the transdermal smart patch; and ii) provide access to the data corresponding to the signals to either a user to which the transdermal smart patch is applied, or a user administering the transdermal smart patch.

\* \* \* \* \*